United States Patent [19]
Winslow et al.

[11] Patent Number: 5,947,899
[45] Date of Patent: Sep. 7, 1999

[54] COMPUTATIONAL SYSTEM AND METHOD FOR MODELING THE HEART

[75] Inventors: Raimond Winslow, Timonium, Md.; Donna Rounds, New York, N.Y.; David Scollan, Baltimore, Md.

[73] Assignee: Physiome Sciences, Princeton, N.J.

[21] Appl. No.: 08/703,603

[22] Filed: Aug. 23, 1996

[51] Int. Cl.$^6$ .................................................. A61B 5/00
[52] U.S. Cl. ..................... 600/410; 600/407; 600/508; 128/920; 395/120
[58] Field of Search ............................... 128/653.1, 653.2, 128/696, 699, 731, 920, 922, 923; 395/120, 924; 600/407, 410, 508, 512, 544

[56] References Cited

U.S. PATENT DOCUMENTS

| | | | |
|---|---|---|---|
| 5,228,443 | 7/1993 | Tatar | 128/653.2 |
| 5,392,210 | 2/1995 | Scholz . | |
| 5,435,310 | 7/1995 | Sheehan et al. | 128/653.1 |
| 5,594,849 | 1/1997 | Kuc et al. | 395/135 |
| 5,601,081 | 2/1997 | Tomita et al. | 128/653.1 |
| 5,634,469 | 6/1997 | Bruder et al. | 128/699 |

OTHER PUBLICATIONS

Cai, D. et al., "Effects of Gap Junction Conductance on Dynamics of Sinoatrial Node Cells: Two–Cell and Large–Scale Network Models", *IEEE Transactions on Biomedical Engineering*, vol. 41, No. 3, pp. 217–231 (Mar. 1994).
Holden, A. V., et al. "Reconstructing the Heart", *Chaos, Solitons & Fractals*, vol. 5, Nos. 3/4, pp. 691–704 (1995).
Noble, D., "The Development of Mathematical Models of the Heart", *Chaos, Solitons & Fractals*, vol. 5, Nos. 3/4, pp. 321–333 (1995).
Panfilov, A., Re–entry in an Anatomical Model of the Heart, *Chaos, Solitons & Fractals*, vol. 5, Nos. 3/4, pp. 618–689 (1995).
Winslow, R. L., et al, "Simulating cardia sinus and atrial network dynamics on the Connection Machine", *Physica D*, 64, pp. 281–298 (1993).
Black, S. C., et al., "Potassium channel openers are likely to be proarrhythmic in the diseased human heart", *Cardiovascular Research*, pp. 923–924 (1994).
D'Alonzo, A. J., et al., "Potassium channel openers are unlikely to be proarrhythmic in the diseased human heart", *Cardiovascular Research*, pp. 924–929 (1994).
Kääb, S., et al., "Ionic Mechanism of Action Potential Prolongation in Ventricular Myocytes From Dogs With Pacing–Induced Heart Failure", *Circulation Research*, vol. 78, No. 2, pp. 262–273 (Feb. 1996).
Kohl, P., "Mechano–electric feedback: Impact on heart rhythm", *Futura*, pp. 240–252 (Apr. 1995).
Kohl, P., et al., "Mechanosensitive connective tissue: potential influence on heart rhythm", *Cardiovascular Research* 223 (1996).
Shipley, J. B., M.D., et al., "Inotropic Therapy for the Failing Myocardium", *Clin. Cardiol.*, 18:615–619 (1995).
Tomaselli, G. F., M.D., et al., "Sudden Cardiac Death in Heart Failure", *Circulation*, 90:2534–2539 (Nov. 1994).
Wilde, A. A. M., et al., "Electrophysiological effects of ATP sensitive potassium channel modulation: implications for arrhythmogenesis", pp. 16–24.

*Primary Examiner*—Marvin M. Lateef
*Assistant Examiner*—Shawna J. Shaw
*Attorney, Agent, or Firm*—Beck & Tysver

[57] ABSTRACT

A computational model for simulating and predicting the electrical and chemical dynamics of the heart. The model consists of a computerized representation of heart anatomy and a system of mathematical equations that describe the spatio-temporal behavior of biophysical quantities such as voltage at various locations throughout the heart. The computer process can present the temporal evolution of the biophysical quantities throughout the computerized anatomical model.

34 Claims, 9 Drawing Sheets

FIG. 6A

| MEMBRAN POTNTIAL | |
|---|---|
| I. | $V = -1/C(1_i + 1_{PUMP})$ |
| PUMP CURRENTS | |
| II. | $I_{PUMP} = f([C_k)_0 \cdot [C_k]_i V)$ |
| VOLTAGE GATED IONIC CURRENTS | |
| III. | $I_i = (V-E_i)G_i(V)$ <br> $= (V-E)G_i m_i(V)^P h_i(V)^q$ <br> WHERE <br> $m_i(V) = [m_i(V) - m_i(V)]_i^{m(V)-1}$ <br> $h_i(V) = [h_i(V) - h_i(V)]_i^{h(V)-1}$ |
| IONIC CONCENTRATIONS | |
| IV. | $[C_k] = -I_k/ZFV_{eff}$ |

FIG. 6B

| V | TRANSMEMBRANE POTENTIAL |
|---|---|
| m | Na CURRENT FAST ACTIVATION |
| h | Na CURRENT FAST INACTIVATION |
| d | Ca CURRENT ACTIVATION |
| f | Ca CURRENT INACTIVATION |
| x | DELAY OUTWARD RECTIFIER CURRENT ACTIVATION |
| q | TRANSIENT OUTWARD K CURRENT ACTIVATION |
| r | TRANSIENT OUTWARD K CURRENT INACTIVATION |
| (Na)i | INTRACELLULAR Na CONCENTRATION |
| (K)i | INTRACELLULAR K CONCENTRATION |
| (Ca)i | INTRACELLULAR Ca CONCENTRATION |
| (Ca)up | Ca CONCENTRATION IN SARCOPLASMIC RETICULUM UPTAKE POOL |
| (Ca)rel | Ca CONCENTRATION IN SARCOPLASMIC RETICULUM REALEASE POOL |
| (Ca)calmod | CONCENTRATION OF Ca BOUND TO CALMODULIN BUFFER |
| (Ca)trop | CONCENTRATION OF Ca BOUND TO TROPONIN |
| factivator | FRACTION OF Ca CHANNELS WHICH ARE ACTIVATED |
| fproduct | FRACTION OF Ca CHANNELS IN WHICH THE Ca REGULATORY SITE IS NOT OCCUPIED AND WHICH HAVE NOT YET UNDERGONE INACTIVATION |

FIG. 6C

| | |
|---|---|
| INa | FAST INWARD Na CURRENT THAT INITIATES THE ACTION POTENTIAL. |
| IK | DELAYED OUTWARD RECTIFIER CURRENT THAT CONTROLS THE INITIAL PHASE REPOLARIZATION AND INFLUENCES ACTION POTENTIAL DURATION. |
| IK1 | INSTANTANEOUS OUTWARD K CURRENT THAT DETERMINES THE ACTION POTENTIAL THRESHOLD AND INFLUENCES LATER PHASES OF REPOLARIZATION. |
| Ito | TRANSIENT OUTWARD CURRENT THAT EFFECTS THE SHAPE OF THE ACTION POTENTIAL NOTCH AND EFFECTS ACTION POTENTIAL DURATION. |
| Isi | SECOND INWARD CURRENT WITH CHARGE CARRIED BY Ca, K AND Na IONS. |
| IbK, IbNa IbCa | SMALL LINEAR BACKGROUND CURRENTS THAT CONTRIBUTE TO THE CELL RESTING POTENTIAL, ACTION POTENTIAL THRESHOLD, AND ACTION POTENTIAL DURATION. |
| INa,K | ENERGY REQUIRING Na-K PUMP CURRENT WHICH EXTRUDES Na IONS FROM THE INTERIOR OF THE CELL IN ORDER TO MAINTAIN A LARGE Na CONCENTRATION GRADIENT ACROSS THE ELL MEMBRANE. |
| INa,Ca | THE Na-Ca EXCHANGE CURRENT THAT EXTRUDES Ca THAT HAS ENTERED THE CELL DURING THE ACTION POTENTIAL. |
| Iup | CURRENT THROUGH AND ENERGY REQUIRING PUMP WHICH MOVES Ca IN THE CYTOSOL INTO THE SARCOPLASME RETICULUM AND HELPS LIMIT ACTION POTENTIAL DURATION AND THE DURATION OF CONTRACTION SUBSEQUENT TO THE ACTION POTENTIAL. |
| Itr | A TRANSFER CURRENT THAT REPRESENTS THE MOVEMENT OF Ca IONS FROM NON-JUNCTIONAL SARCOPLASIC RECTICULUM. |
| Irel | THE Ca CURRENT RELEASED FROM SARCOPLASMIC RETICULUM DURING THE ACTION POTENTIAL. THE RAPID ACCUMULATION OF Ca IN THE CELL DUE TO THIS CURRENT TRIGGERS MUSCLE CONTRACTION. |

COMPUTATIONAL SYSTEM AND METHOD FOR MODELING THE HEART

TECHNICAL FIELD

The present invention constitutes a computing system and software model of a physical organ, and more particularly to processes and procedures for generating a biophysically detailed, predictive model of the mammalian heart which accepts anatomic and biophysical data and generates a representation of the electrophysiologic state of the heart.

BACKGROUND ART

Physiologic organs consist of various types of cells organized into tissues. These tissues form an organ, which in turn interacts with the whole body. The ability to model organ function with a high level of biophysical, biochemical, and structural detail is of enormous value to biology and medicine, because such models provide deep insight into the cause of disease.

Given the immense complexity of even the simplest organ, the principal task that confronts the model builder is to recognize what biophysical detail can be successfully disregarded in constructing a computationally useful model.

The heart for example includes a sino-atrial node and atrio-ventricular node, as well as the bundle of His and the Purkinje fiber system. These structures have a profound impact on the electrical activation sequence of the heart muscle fibers within the atria and ventricles, and thus have an enormous impact on the heart's mechanical function. It is well known that organic and anatomic defects in these structures can result in life-threatening cardiac arrhythmias. A model that allows a user to interact with an accurate and predictive model of the heart's cells and tissues would be of great value.

This objective has spurred the development of computational models of cardiac cells and tissues. These computational models have sought to integrate experimental observations and theoretical knowledge into a formal model expressed in mathematical terms. Various algorithms, processes and procedures are used to describe the behavior of the cells and tissues that comprise the organ system. A useful computer-implemented model should effectively emulate interesting behaviors.

The earliest mathematical models of the heart used formal mathematical assumptions about cellular physiology; for example Van der Pol and Mark's description of the heartbeat as a relaxation oscillator in 1928. Real physiological parameters were not included in models until 1952 when Hodgkin and Huxley explained their observations on the action potential of the giant squid axon in their classic work on membrane processes and ion fluxes. The success of their work can be measured by the many models that have followed their paradigm to model systems as diverse as neurons, cardiac cells, pancreatic beta cells, and other excitable cells. One descendent model was the 1962 Noble model of the cardiac Purkinje fiber which was based on experimental evidence that two potassium conductances, together with a sodium conductance, are sufficient to generate action potentials and pacemaker potentials.

Technical innovations have led to more precise experimental data which in turn has led to the ongoing refinement of models as new information has been incorporated. The result has been that the accuracy and predictability of models have been upgraded with respect to actual biophysical and physiological parameters; for example, beginning with the Noble model of the Purkinje fiber, subsequent experiments extended the description of cardiac electrophysiology to include more refined models of the Purkinje conducting system, as well as sinus node, atrial, and ventricular cells. These single cell models have evolved, through successive improvements and refinements, into a software package called "OXSOFT HEART 4.5" presently available to investigators under license from Takhus, Inc.

Presently the "OXSOFT" model is restricted to the modeling of cardiac function at the single cell (or "zero-dimensional") level. This model incorporates mathematical expressions that represent the biochemical, biophysical, and cellular mechanisms (Hodgkin-Huxley) within single cardiac cells. These equations collectively define a given cardiac-cell state.

The "OXSOFT" models require the solution of thirty or more simultaneous non-linear differential equations. Even on the fastest personal computers it can take several minutes to compute only a few seconds of activity. Nonetheless zero-dimensional models have proven to be successful not only in reproducing normal single cell cardiac electrical activity, but also in reconstructing some of the cellular mechanisms of arrhythmia, including ectopic beating and the effects of therapeutic drug administration (e.g., cardiac glycosides). These models can exhibit the action potential shortening during ATP depletion, and the early after-depolarizations characteristic of potassium blocking compounds and calcium agonists observed in actual hearts. Initial success has prompted researchers to try to extend the dimensionally of these models but just how best to do this has remained elusive.

To date, efforts to extend the single cell models and to develop large scale higher dimensional models usually have favored simplicity, flexibility, and computational efficiency. While these characteristics make it possible to simulate large systems for extended periods, it requires that biophysical and biochemical mechanisms essential to the explanation of arrhythmias be extrapolated and rule driven. Extrapolation of the essential mechanisms governing real systems is done by guesswork and, to some extent is justified only when basic rules have been tested in simulation. Such models are not usefully predictive.

Some limitations of existing 1-D and 2-D models have been eliminated by development of a software packages called "SA" and "VENT", licensed to Physiome Sciences Inc. These one- and two-dimensional network models of the mammalian sino-atrial node, atrium, and ventricles incorporate all of the biophysical detail described within the "OXSOFT" single cell models, but also account for cell to cell propagation of electrical activity within simple cardiac cell networks. When 1-D and 2-D models are iterated by the computer, the state of the various nodes change, giving rise to data that expresses the propagation of electric wave fronts in the model. However the 2-D model's electrophysiological wave front characteristics do not accurately mimic the complex characteristics of actual arrhythmias.

Many laboratories value this work but existing versions of Oxsoft HEART, AS, and VENT (1-D and 2-D network models) neither simulate nor accurately predict the heart's three-dimensional electrophysiological behavior.

SUMMARY DISCLOSURE OF INVENTION

In contrast to prior models, the present model renders detailed three-dimensional information about the heart based on cell function. The present invention is a composite of procedures that, through interaction, permits three dimensional electrophysiological simulation of the heart, commonly referred to as the "3-D heart" model.

The model computationally represents cardiac anatomy and a system of mathematical equations describing the spatio-temporal behavior of biophysical quantities such as cardiac voltages at various locations. The computer processes combines these two parts of the model in a simulation presenting the temporal evolution of the state defining quantities in the anatomical model.

The preferred finite difference expression of the computerized anatomical model consists of a set of N nodes that are arrayed in a three-dimensional network. Each node corresponds to a region of tissue within the heart. And each node has at least five neighbors. This region of tissue may be defined as follows: a) a segment of an individual cardiac cell; b) an entire cardiac cell; c) a small region of cardiac tissue consisting of more than one cell.

Regardless of how a node is defined, each node communicates with its neighbors. This communication reflects electrical coupling between adjacent parts of cells, cells, or groups of cells within the heart. In an actual heart the coupling strength depends on local anatomy. Thus the network level description the coupling strength between nodes allows one to encode or model the heart's anisotropic anatomic detail.

Thus the anatomical and biophysical portions of the model constructed and then they are passed to a solution procedure, along with a file that specifies the initial state of the heart.

The model's organization and structure facilitates computation on multiprocessor computers because the nodes engage only in near-neighbor interactions. Therefore the updating process for a large number of locally coupled nodes can be easily segmented and assigned to a single processor. This specific approach enables reasonable processing times for large numbers of nodes, and so resolves the fundamental problem of prior art large-scale biophysically detailed models which are computationally intractable.

BRIEF DESCRIPTION OF THE DRAWINGS

Throughout the several figures identical reference numerals indicate identical structure, wherein:

FIG. 6a is a table setting forth preferred set of node equations;

FIG. 6b is a table setting forth preferred set of node equations;

FIG. 6c is a table setting forth preferred set of node equations;

DETAILED DESCRIPTION

Overview

The composite model includes both "nodes" and a complimentary "network". The network reflects and represents the anatomical structure of the heart; the nodes reflect the spatio-temporal evolution of the nodes' biophysical quantities.

Therefore at each node of the model, various biophysical quantities and their related equations are defined. This biophysical model along with the anatomical network is used by the solution program to compute the evolution of the biophysical quantities defined at the nodes. In this manner the electrophysiology of the whole heart can be modeled.

Description of the Computerized Anatomical Portion of the Model

Figure 1:
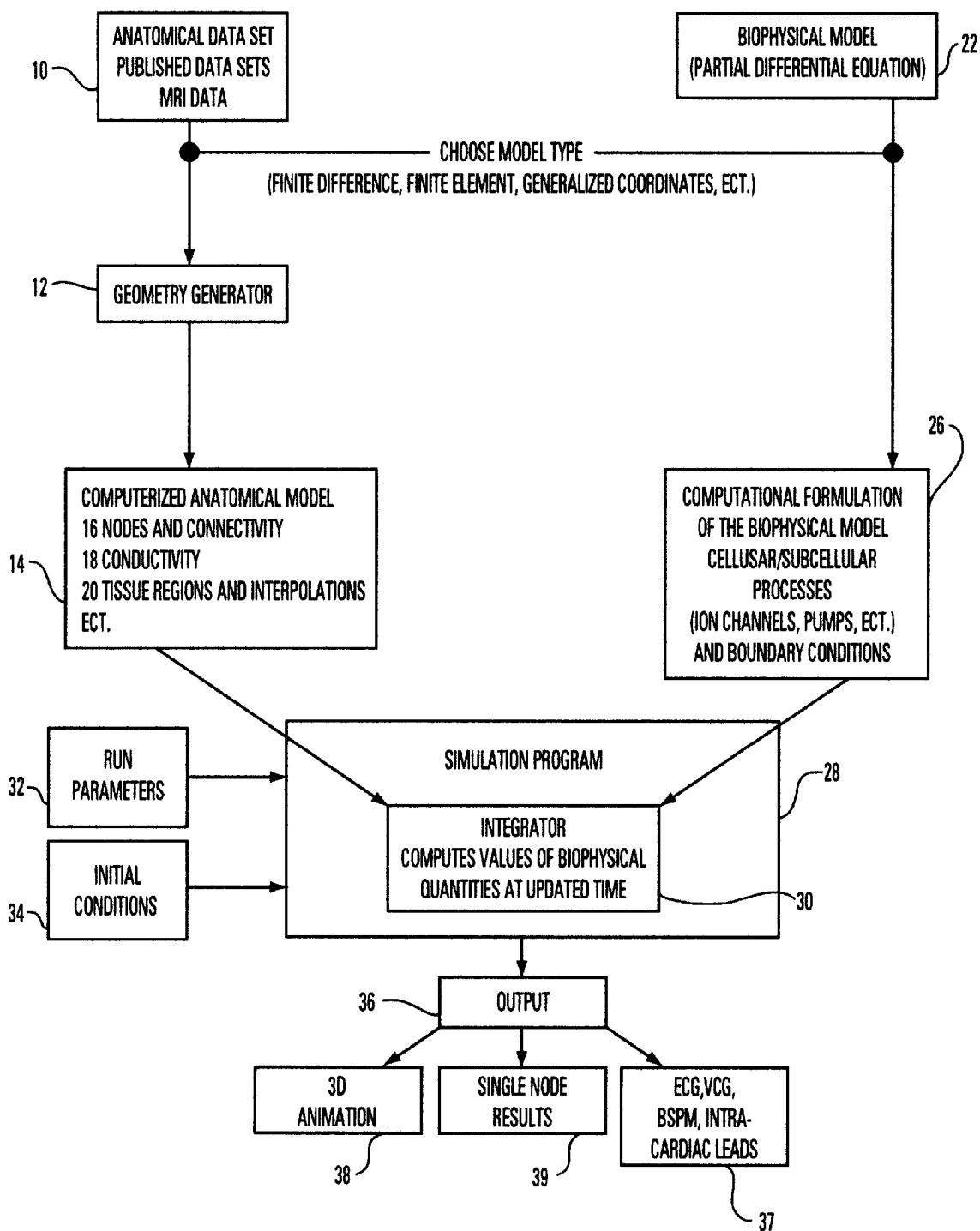
FIG. 1 is representation of the model depicting the organization of the software processes.

FIG. 1 represents the composite model and illustrates procedures for modeling the heart.

At process 10 the heart's anatomical detail is extracted from the heart and communicated to the geometry generator 12. Two ways to acquire anatomic data sets are these: published data sets that have been created by careful dissection of hearts and data derived from magnetic resonance imaging of the heart. However anatomic data sets can come from any of several sources.

Geometry generator 12 creates a computerized anatomical model of the heart represented by object 14. The exact form that anatomic model object 14 assumes depends upon the type of generation process. The finite difference modeling technique is shown in the specification and drawings but finite element and multigrid models are contemplated within the scope of this disclosure.

Figure 2:
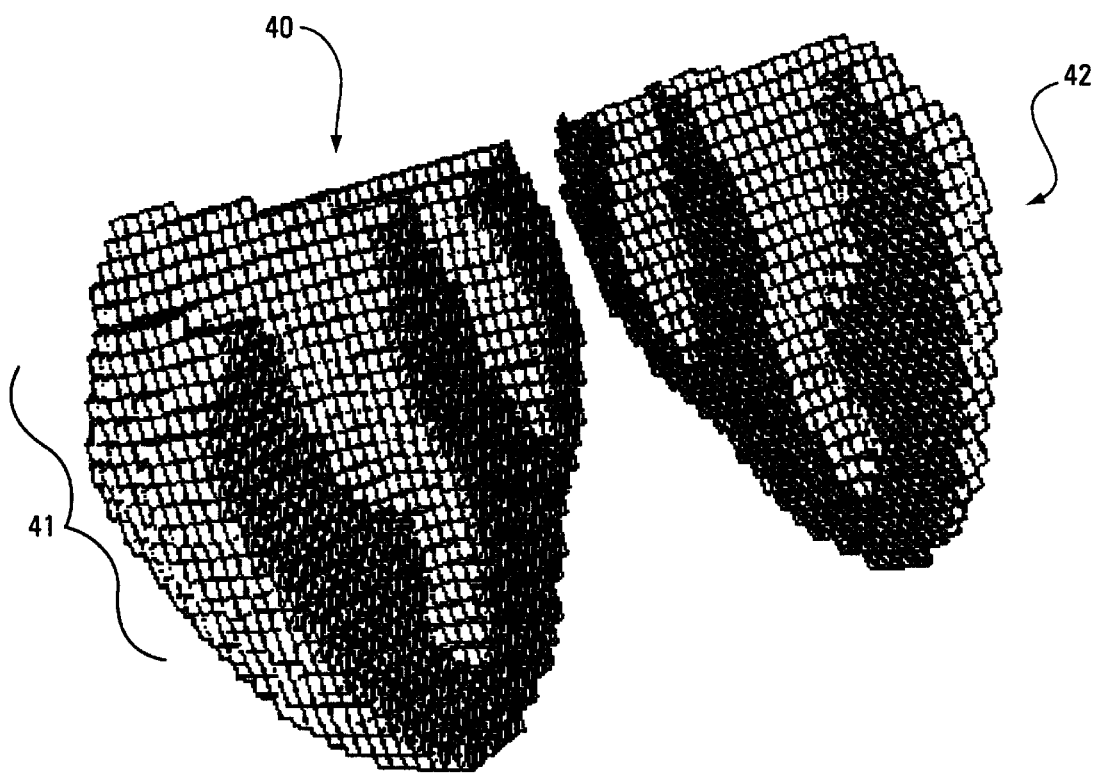
FIG. 2 is a representation of the ventricles of the heart represented in the form of a finite difference network.

In the preferred development, process 12 is used to construct a finite difference anatomic representation of the heart which is best illustrated in FIG. 2 which shows a finite difference heart model 40 comprised of a lattice 41 of nodes typified by node 46.

The node locations and interconnections are specified by object 16. The conductivity between nodes is modeled by object 18. These conductivity relationships between cells of the mammalian heart are specified by coupling relationships between the nodes of the model. In object 20, nodes representing specific tissue types and how they are coupled to the rest of the heart are specified. For example, a set of nodes and their coupling relationships could be modified to represent Purkinje fiber cells, thus representing the physical extent and direction of Purkinje fibers within the myocardium. Object 20 is used in this fashion to capture tissues like these in the model. Object 14 corresponds to the finite difference heart model 40 shown in FIG. 2. This portion of the model is combined with the biophysical model in the simulation program 28.

FIG. 2 depicts a finite difference network of the ventricles of a heart 40 with a portion 42 of the heart cleaved away to show the endocardial surfaces and the chamber geometry. It should be recognized that the set of nodes forms a lattice 41. The figure also shows that the nodes typified by node 44 lie on or in the myocardium and that no nodes are present in the chamber proper.

This figure illustrates a direct relationship between each node and its corresponding spatial location in the heart depicted in the completed lattice 41. One should observe that when a finite difference geometry generator process 12 is used, the nodes form a cubic lattice structure with each node having at least five (and more commonly six) near neighbors.

Figure 3:
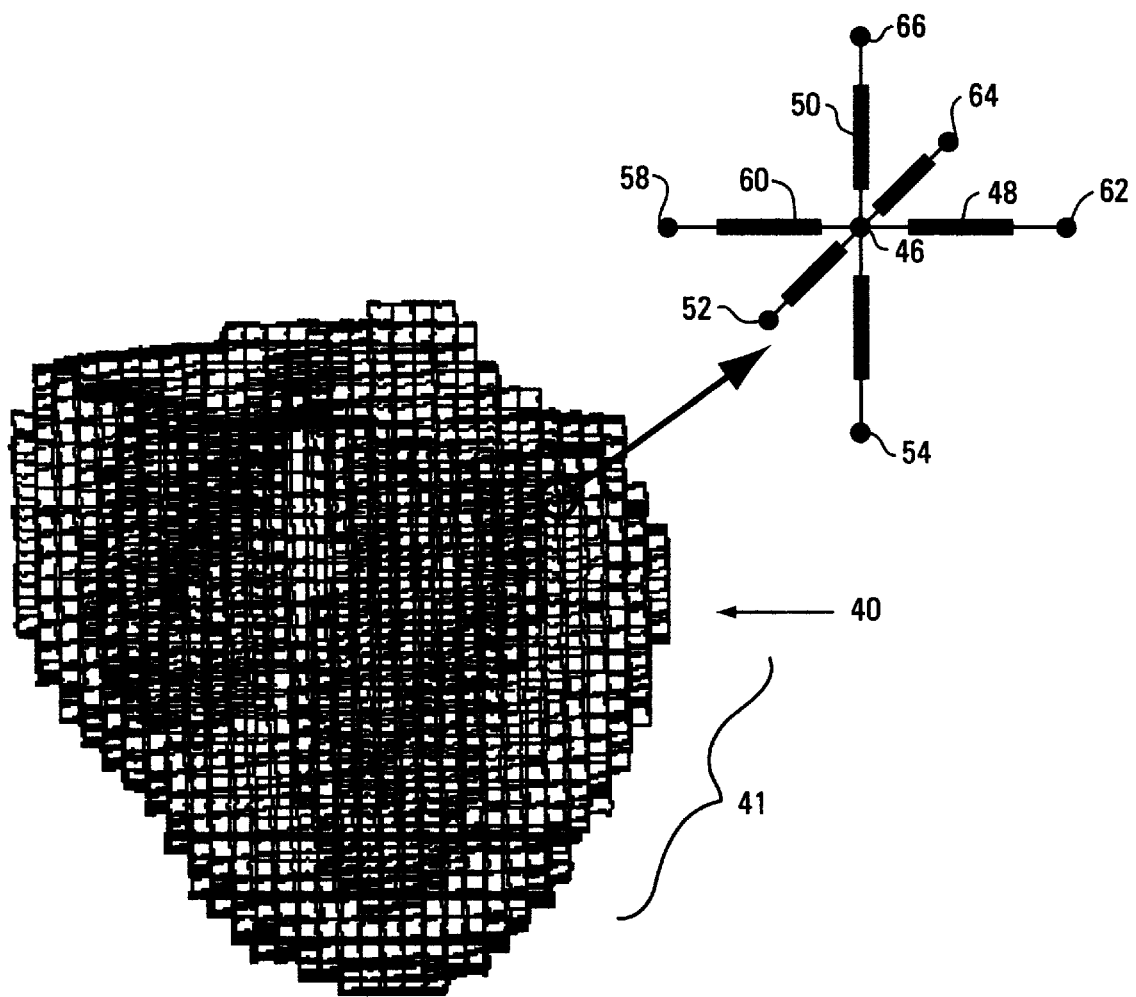
FIG. 3 is a representation of the model depicting the organization of nodes and coupling relationships.

FIG. 3 shows a subject node 46 extracted from the finite difference model of the myocardium and presented with its near neighbors. The lattice 41 reveals three global orthogonal axes. The X-axis 48 and Y-axis 50 and Z-axis 52, pass through an origin which is occupied by the subject reference node 46. The coupling relationship between node 46 and its companions is shown as a block typified by block 60 connecting node 46 with node 58. The anisotropy of the heart as taken from the anatomic data set 10 is used to define each of the many relationships illustrated by coupling relationship depicted by block 60. In general the tensor of the anatomic data will be resolved into the three orthogonal axes shown on the figure. This figure is intended to show the computational coupling relationship between nodes such as node 58 and node 46. In general the coupling relationship between nodes depends on both cell type and cell orientation.

For example, in the heart, conductivity between adjacent cells is strongest in the direction of the long axis of each cell (cardiac cells are typically long and thin). This direction is known as the fiber orientation. Fiber orientation changes throughout the myocardium, thus varying from node to node in the model. In the 3-D heart model, coupling strength between each node is varied according to these spatial changes of fiber orientation. Thus, the lattice parameters (coupling strength), which control the communication of data between cellular nodes is used to encode the detailed anatomical structure of the heart model. This coupling relationship is a part of the object 14 and is represented by object 18.

Computation of the spatial dependency of voltage depends on determining the electrical current flow between adjacent nodes of the lattice, because a triggered depolarization results when current flows into a node from an adjacent node. This current flow is simulated in simulation program 28 by using Ohm's Law. Defining VA and VB as the transmembrane voltages at node 58 and 46 (FIG. 3), and G as the coupling conductance (i.e., inverse of resistance) between these two nodes, then the coupling current flowing from node 46 to node 58 is given by $$I = G^*(VA - VB).$$

Thus, in order to compute the coupling current I between any pair of nodes typified by node 46 and node 58 it is sufficient that the nodes communicate only their transmembrane voltages to each other. Communication in the model is therefore local. G may be a constant linear conductance, or it could be given by a biophysically accurate model of properties of cardiac gap junction channels. The transmembrane voltages are discussed in the following section.

Description of the Biophysical Portion of the Model

Figure 4:
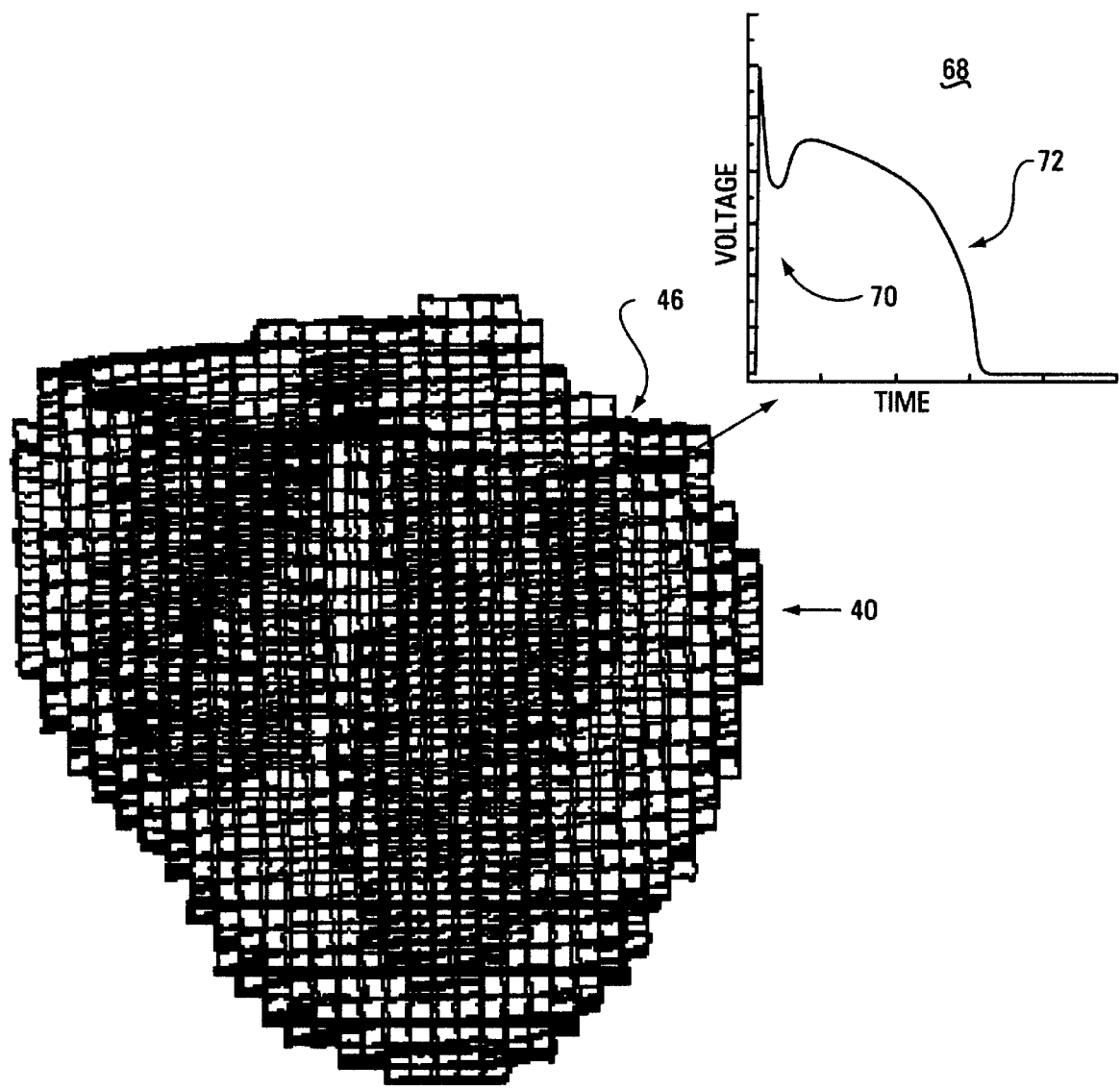
FIG. 4 is a representation of the action potentials which result from the set of equations associated with each node.

FIG. 4 is similar to FIG. 3 in that it shows a representative node 46 of the heart 40. In this representation the node 46 is associated with chart 68 which depicts a computed action potential at the node. The action potential is the biologic term used to denominate the time course or evolution of cellular voltage. All cells have a potential difference between the interior of the cell and the exterior of the cell. This so called transmembrane potential results from the accumulation of negatively charged ions within the cell. In the case of physical excitable cells, ion channels in the membrane open and close sequentially which allows the ions to migrate across the membrane results in the depolarization portion of the wave form shown as intrinsic deflection 70. In this phase the rapid sodium (Na) channels open. This sharp change in voltage is communicated to the near neighbor cells, triggering a depolarization in the adjacent cells. Metabolic processes then commence to repolarize the cell. The return to the resting potential is shown in the action potential table 68 by curve 72.

Again referring to FIG. 1, once the object 14 has been defined and created, the biophysical model 22 must be specified. First, a choice is made of what biophysical quantities are of interest. Next, a mathematical model that describes their spatio-temporal behavior is developed in process 26. Usually these processes can be described in the form of partial differential equations. These equations describe the cellular and subcelluar processes that determine the values of the biophysical quantities from one moment in time to the next. Then this mathematical model must be translated into a computational form by process 26 so that the solution program of process 28 can use the process 26 as a subroutine. The structure of this simulation program 28 will depend upon what type of anatomical model was constructed—i.e., a finite difference anatomical model demands a finite difference representation of the biophysical model.

The biophysical model 22 (FIG. 1) includes in a set of N×Neq coupled (through voltage) nonlinear ordinary differential equations (ODEs), with coupling as defined by the anatomical model. Given initial values 34 for the state variables defined by each of these equations (referred to as an initial condition), and given boundary conditions on electrical current flow at the bounding surfaces of the model, these ODEs may be evolved in time to predict electrical activity within the heart. The ability to relate this predicted electrical activity to cellular electrophysiology is the single most useful characteristic of this model.

Representative equations for defining the state of the node are set forth in tables in FIG. 6a; FIG. 6b and in FIG. 6c. They include: voltage dependent transmembrane currents for (Na), (K), and (Ca) ionic species; transmembrane ion pump currents for (Na), (K), and (Ca) ionic species; total transmembrane flux of (Na), (K), and (Ca) ionic species; total transmembrane ion flux in cellular organelles; each node having a total transmembrane flux due to lipid bilayer membrane capacitance.

In the preferred and illustrative finite difference development, the partial differential equations reduce to a set of ordinary differential equations defined at each node. These equations define the biophysical processes giving rise to the unique properties of cardiac tissue. In general, this system includes: a) equations defining properties of nonlinear, voltage-gated transmembrane currents; b) equations describing properties of ion pumps and exchangers in the cell membrane; c) equations describing the buffering, uptake, storage, transfer, and release of calcium ions by intracellular organelles; and d) equations describing time-varying changes of intracellular ion concentration.

FIG. 6a sets forth exemplary equations while the tables of FIG. 6b and FIG. 6c identify a grouping of biophysical processes that are suitable for use in the preferred model. These table may be related to the action potential of FIG. 7. The corresponding ionic current flows are associated with the time course of FIG. 7.

With respect to FIG. 1, the simulation program 28 interatively computes the action potential defining equations from the biophysical model 22 for all the nodes and additionally computes the contribution that near neighbors have on the voltage at the nodes. This process is represented in the figure by integration process 30. The initial conditions are presented to the simulation process 28 by the object 34 which is typically a data file. In a similar fashion the run parameters are presented by a data file shown as object 32. The output 36 of the simulation program 28 can be expressed in any one of a number of ways. One very useful output format is a 3D animation of the time course of voltage over several heartbeats. Normally the animation is created by a graphics terminal dedicated to animating large data files. Single node results are also available and may be presented in the form of computed action potentials.

Figure 5:
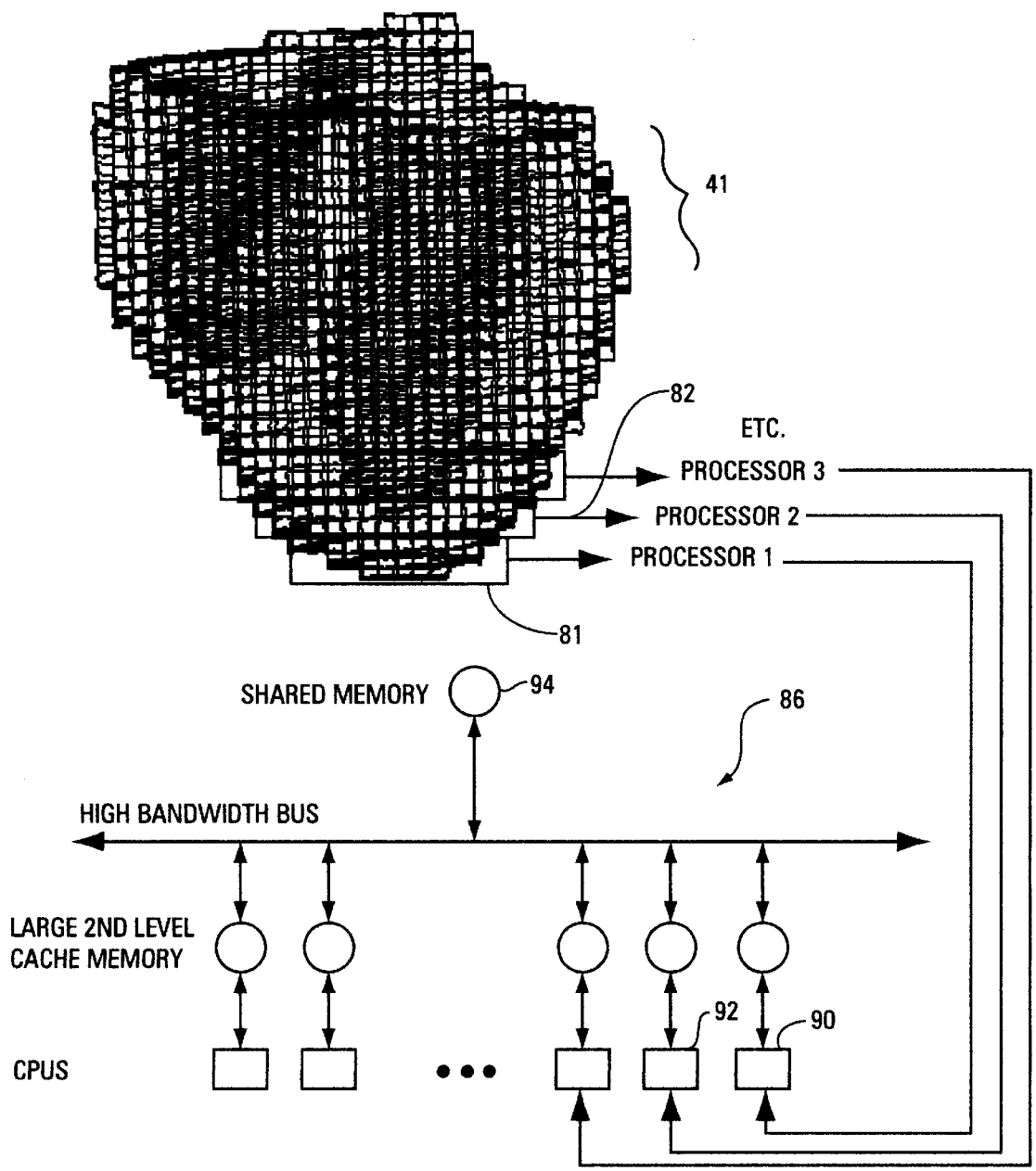
FIG. 5 is a representation of the model depicting the relationship between the organization of an illustrative computer system with the model.

FIG. 5 among other things illustrates a parallel processor computer system 86. The operating system software can select a set of nodes 81 and have the state equations run on a single processor 90. A separate set of nodes 82 can be concurrently computed on processor 92. In this fashion the state defining equations at the nodes can calculated simultaneously. The fact that the state of each node is essentially local renders this approach practical. Once the action potentials of all nodes is completed the appropriate state data can be accumulated in the shared memory 94. With this data available the individual processors can next compute the coupling relationships giving rise to the output 36 (FIG. 1).

Various graphical display techniques can be used to present this data to the user including 3D animation 38, single node action potential results 39 or simulated surface presentations 37.

Figure 7:
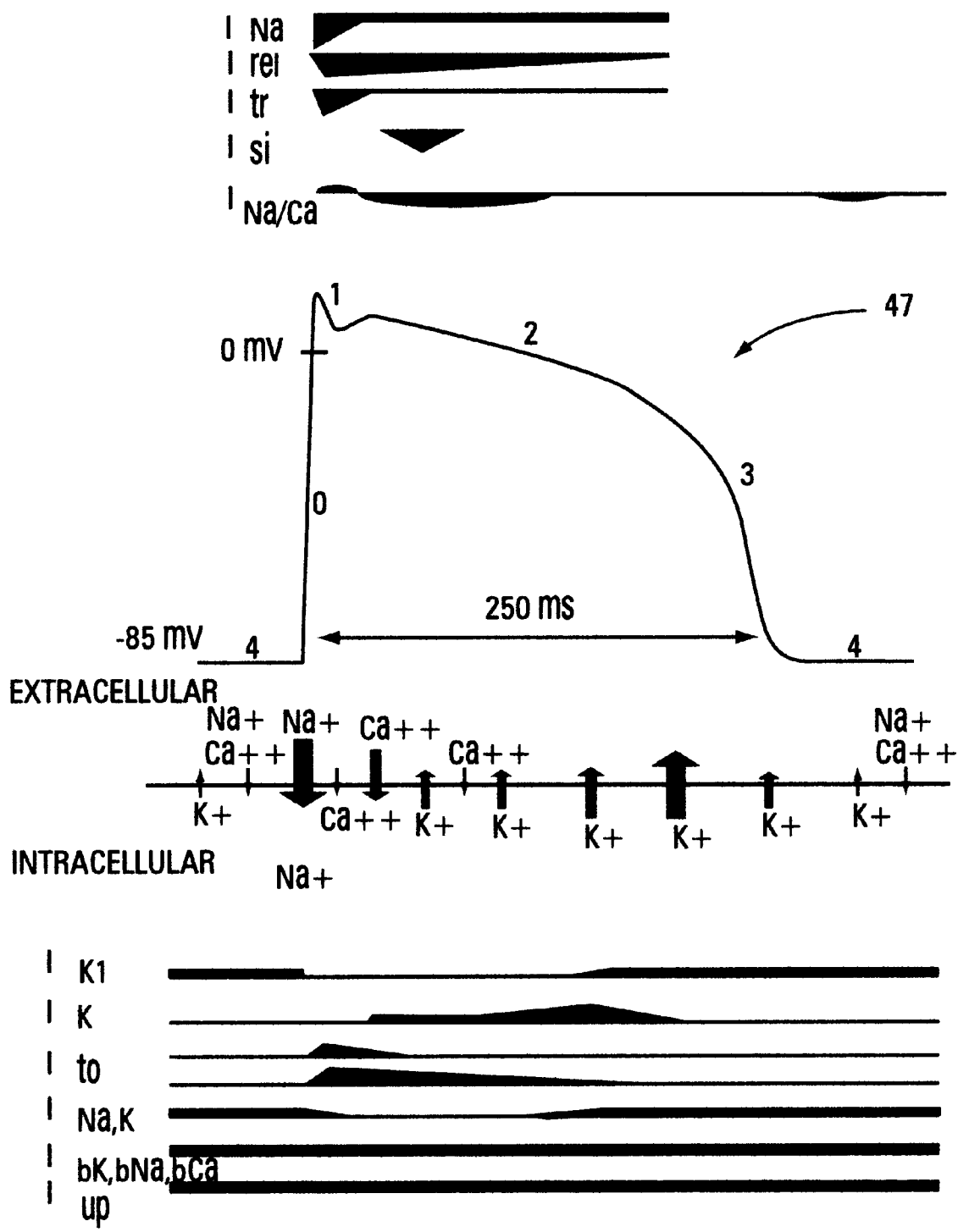
FIG. 7 is a representation of a computed action potential along with corresponding membrane currents.

FIG. 7 shows a computed-action potential for a single node. By convention, the action potential is broken into several phases: the resting potential corresponds to Phase 4; the rapid depolarization of the cell across the membrane is represented by Phase 0; Phases 1 and 2 correspond to a depolarization plateau; and Phase 3 corresponds to the return of the node to the quiescent state.

The action potential of cardiac cells has been the subject of intense study, and it should be appreciated that the time course of the potential shown in FIG. 7 is the result of various ionic transfers shown in FIG. 7. The initial in-rush of calcium and sodium gives rise to the loss of potential difference between the extra-cellular and intra-cellular space. This process induces voltage-gated ionic current, which gives rise to Phase 3 of the figure. Thus, the time course of the voltage is taken as the sum of the Phase 0 through Phase 4 currents. Although the currents depicted in FIG. 6(a), 6(b), and 6(c) are preferred, the precise formulation of the currents are subject to further refinement as additional experimental evidence becomes available. Further detail related to these specific currents can be found in the Oxsoft documentation.

The above specification, examples and data provide an illustrative description of the invention. Since many embodiments of the invention can be made without departing from the spirit and scope of the invention, the invention resides in the following claims.

What is claimed is:

1. A computational model of a heart comprising:

a space defining a lattice having a set of nodes;

each of said nodes positioned in said lattice such that each node is adjacent to neighboring nodes;

whereby said lattice and node together define a three dimensional representation of at least a portion of the heart;

each node of said set of nodes representing a unit of the myocardium;

each node having a associated with it a set of state defining node equations for computing an action potential at the location of said node and for computing a node potential;

each node having associated with it a set of coupling relationships related to the anisotropic anatomic structure of the heart for computing the contribution to said node potential contributed by neighboring nodes;

whereby a total set of voltages at each of said nodes represents the global depolarization state of the heart.

2. A computational model of a heart comprising:

a cubic lattice having a set of N nodes;

each of said nodes positioned at a vertex of said lattice;

each node representing a biophysical computational unit of the heart;

each node having associated with it a set of state defining equations expressing state variables sufficient to compute node response at the next instant in time $t+\delta t$ given node response at time t, said equations including at least one equation selected from biophysical processes selected from the set:

i) equations for time-varying, voltage-dependent transmembrane conductances permeable to ions, the temporal evolution of which are modeled using ordinary differential equations;

ii) equations for time-varying transmembrane ionic pump and exchanger currents, properties of which are modeled using algebraic equations;

iii) equations for time-varying Ca uptake, sequestration, and release currents modeling the regulation of intracellular Ca levels by cellular organelles, the properties of which are modeled using coupled systems of ordinary differential equations;

iv) equations for total transmembrane flux of each ionic species to which the cell membrane is permeable;

each node connection to neighboring nodes represented by an anisotropic coupling conductance, the value of which is defined by the anatomic relationship of the two nodes;

each node having a coupling current associated with it determined by the total current entering the node through all said coupling conductances defined at that node;

whereby said coupling currents and node state equations may be solved for the temporal evolution of all state variables at all nodes.

3. A method for computing a model of a heart comprising the steps of:

a) defining a set of lattice nodes;

each lattice node representing a biophysical subunit of the heart;

each node having a set of biophysical equations for computing a total node current associated with ion transport in said biophysical subunit;

each node associated with at least five adjacent nodes;

each node coupled to neighboring nodes;

said coupling modeled as an anisotropic resistance;

b) solving said set of biophysical equations to determine said node currents;

c) summing said node current to determine the voltage present at each node resulting from the depolarization of each neighboring node;

d) displaying a representation of said computed voltage.

4. A method for modeling a heart with a computer comprising:

a) defining a set of nodes;

each node representing a biophysical subunit of the heart;

each node having a membrane, defining an intracellular and an extracellular space;

each node having set of biophysical equations associated with it for computing a coupling current associated with ion transport in said intracellular space;

each node having set of biophysical equations associated with it for computing a coupling current associated with ion transport in said extracellular space;

each node having a set of biophysical equations associated with it for computing a transmembrane current between the intracellular and extracellular spaces;

b) defining a lattice including each of said nodes;

each node associated with a physical location in heart tissue;

each node connected with at least five adjacent nodes;

each node exhibiting an anisotropic coupling with neighboring nodes reflecting the anatomic relationship between such nodes;

said coupling modeled as a coupling resistance;

c) solving said set of biophysical equations to determine said node currents associated with extracellular and intracellular currents;

d) summing said node current to compute the voltage present at each node resulting from the depolarization of each node and the propagation of a depolarization wave front through each node;

e) displaying a representation of said computed voltage.

5. A model of a biological organ system comprising:

a plurality of nodes;

each node having associated therewith a set of state defining equations which take as their variables biophysical data, which are substantially local to the node itself;

each node having at least one state variable which takes as its argument parameters communicated solely from near neighbors;

a network containing all such nodes;

said network including anisotropic coupling relationships defined between each node and its near neighbor node wherein said coupling relationships are expressed as a set of state defining equations;

whereby said state defining variables can be solved iteratively and state variable values communicated to the network model, whereby said network equations can be computed for each node.

6. A method of defining a model comprising the steps of:

applying nuclear magnetic resonance imaging to a biological organ to generate a data file defining tensors associated with the distribution of water molecules within the physiologic organ;

applying said tensor dataset to a network to determine the magnitude of coupling conductances between nodes of the network such that the tensor information is reflected by the internodal conduction values of the network, thus embedding the anatomic characteristics of the organ in the model.

7. A method for using a multiple processor computer to solve for the temporal evolution of state variables defining biophysical and biochemical properties of nodes within a network model of a biological system comprising:

partitioning a lattice of nodes making up the network into N number of lattice subsets, such that each node within the network is included in at least one of said subsets;

associating state equations and state variables describing the biophysical and biochemical properties of each node in said subsets with particular processing units in the multiple processor computer such that each subset of nodes is associated with a distinct processing unit, and that all processing units are associated with at least one subset of nodes;

computing the temporal evolution of all state variables within each of the node subsets associated with distinct processing units concurrently across each of the processing units;

concurrently storing said state variables in computer memory;

displaying a sequence of said state variables.

8. A method of modeling a cardiac disease state in a model of a heart as set forth in claim 3 comprising the additional steps of:

e) adjusting the lattice defining the anatomic structure of the heart such that anatomical structural changes known to occur in the heart during said disease state;

f) using said adjusted lattice to determine the magnitude of coupling conductances between nodes of the network such that the altered structure of the heart in the disease state, as represented by the adjusted lattice, is embedded in the network model;

g) adjusting parameters of the set of state defining equations, specifying properties of biochemical cellular processes defined at each node of the lattice, to reproduce changes in these parameters known to occur in said disease state;

h) adjusting initial values of state variables, the temporal evolution of which is determined by the set of equations specifying properties of biochemical cellular processes defined at each node of the lattice, in such a way as to reproduce changes in these state variables known to occur in said disease state;

i) solving for the temporal evolution of state variables, defined at each node of the lattice;

j) storing said state variables in a computer memory for graphical display and analysis.

9. A computational model of a heart comprising:

a computing device having computational and storage mechanisms;

a set of n nodes arranged in a cubic lattice stored in the storage mechanism, with each node having at least five neighbors;

each node having a set of state variable equations associated with it;

said equations describing biophysical and biochemical reactions at each node which may be solved to find the currents present at each node;

the lattice having a set of anisotropic coupling equations associated therewith defining the coupling between each node, which may be solved by the computational mechanism to determine the total voltage present at each node in the lattice to be stored in the storage mechanism.

10. A finite-difference computational model of a heart comprising:

a) a computer having memory;

b) a set of N nodes arranged in a cubic lattice stored in the memory with each node having at least five neighbors;

c) a subroutine procedure executable on the computer which uses experimentally measured data on fiber orientation within the heart for computing the connection currents between lattice nodes;

d) a multi-dimensional data array with individual elements F(N1,N2,N3, . . . S1,S2,S3, . . . SNeq) stored in the memory, the array having several position elements (N1, N2, and N3) specifying the position of each node within the cube lattice; and state variable element Sx specifying the xth state variable for each node, and state variable value elements (S1,S2,S3, . . . SNeq) specifying the value of the SNeq variables at each node at time t;

e) a multi-dimensional data array F(N1,N2,N3,S1-S2-S3- . . . SNeq-) stored in the memory in which the variable Sx' denotes the time rate of change, $dSx(t)/dt$, of state variable x at time t;

f) a subroutine procedure executable on the computer which specifies an algorithm for computing elements of the multi-dimensional data array F(), with this subroutine procedure itself being composed of a number of subroutine procedures selected from a library of procedures corresponding to biophysical processes modeled at the sub-cellular level;

g) a subroutine procedure executable on the computer specifying a numerical integration algorithm for the computation of values of the state variables S1, S2, S3, . . . , SNeq at time t+δt given values of S1, S2, S3, . . . , Sneq and F(N1,N2,N3,S1- S2- S3- . . . SNeq) at time t.

11. A computational model of a heart comprising:

a) a computer having memory;

b) a set of n nodes arranged in a cubic lattice stored in the memory with each node having at least five neighbors;

c) each node having a set of state variable equations executable on the computer associated with it;

d) said state variable equations describing biophysical and biochemical reactions at each node which may be solved to find the currents present at each node based upon local parameters, and the voltages present at each node based upon local and near neighbor parameters;

e) the lattice having a set of anisotropic coupling equations associated therewith that are executable on the computer defining the coupling between each node, which may be solved to determine the total node voltage present at each node in the lattice.

12. A method of computing the model of claim 8 comprising the steps of:

i) partitioning the lattice into m nodes and assigning state variable computations to one of P processing units;

ii) concurrently computing state variables with the P processing units;

iii) computing the temporal evolution of all state variables and storing or displaying the results.

13. A method of computing the temporal evolution of state variables in the model of claim 3 on multiprocessor computers consisting of a set of P processors each with local memory of capacity M bytes, a communications network supporting data exchange between processors, and a global shared memory, with the method comprising the steps of:

e) partitioning the lattice into Q sets of nodes, referred to as node sets, in such a way that all state variable values at time t, parameters, and required temporary storage locations (work space) for any node set fits into the local memory available to any processing unit;

f) assignment of each node set to a specific processing unit and local memory associated with the specific processing unit;

g) inter-processor communication of any data required to compute new values of state variables for nodes positioned at the borders between different node sets;

h) concurrent execution on all P processors of the computations to compute new values of local state variables at time t+δt in each of the node sets that have been assigned to processing units;

i) iteration of steps b) and d) until computation of state variable values at time t+δt, where δt is small, and until all Q node sets are completed;

j) storage of the computed set of state variables on external storage devices for subsequent graphical display;

k) iteration of steps f)–j) until t+δt equals some end time T.

14. A system for modeling a heart with a computer comprising:

a) a means for defining a set of nodes;
each node representing a biophysical subunit of the heart;
each node having a membrane, defining an intracellular and an extracellular space;
each node having set of biophysical equations associated with it for computing a coupling current associated with ion transport in said intracellular space;
each node having set of biophysical equations associated with it for computing a coupling current associated with ion transport in said extracellular space;
each node having a set of biophysical equations associated with it for computing a transmembrane current between the intracellular and extracellular spaces;

b) a means for defining a lattice including each of said nodes;
each node associated with a physical location in heart tissue;
substantially every node connected with at least five adjacent nodes;
each node exhibiting an anisotropic coupling with neighboring nodes reflecting the anatomic relationship between such nodes;
said coupling modeled as a coupling resistance;

c) a means for solving said set of biophysical equations to determine said node currents associated with extracellular and intracellular currents;

d) a means for summing said node current to compute the voltage present at each node resulting from the depolarization of each node and the propagation of a depolarization wave front through each node;

e) a means for displaying a representation of said computed voltage.

15. The system of claim 14 further comprising:

f) a means for modifying one or more of said biophysical equations to reflect the presence of a chemical input.

16. The system of claim 14 comprising:

f) a means for modifying one or more of said biophysical equations to reflect the presence of an electrical input.

17. A method for computing a model of a heart comprising the steps of:

a) defining a set of lattice nodes;
each lattice node representing a biophysical subunit of the heart;
each node having a set of biophysical equations for computing a total node current associated with ion transport in said biophysical subunit;
each node associated with at least five adjacent nodes;
each node coupled to neighboring nodes;
said coupling modeled as a resistance;

b) solving said set of biophysical equations to determine said node currents;

c) summing said node current to determine the voltage present at each node resulting from the depolarization of each neighboring node;

d) displaying a representation of said computed voltage;

e) adjusting the lattice defining the anatomic structure of the heart such that anatomical structural changes known to occur in the heart during said disease state;

f) using said adjusted lattice to determine the magnitude of coupling conductances between nodes of the network such that the altered structure of the heart in the disease state, as represented by the adjusted lattice, is embedded in the network model;

g) adjusting parameters of the set of state defining equations, specifying properties of biochemical cellular processes defined at each node of the lattice, to reproduce changes in these parameters known to occur in said disease state;

h) adjusting initial values of state variables, the temporal evolution of which is determined by the set of equations specifying properties of biochemical cellular processes defined at each node of the lattice, in such a way as to reproduce changes in these state variables known to occur in said disease state;

i) solving for the temporal evolution of state variables, defined at each node of the lattice; and j) storing said state variables in a computer memory for graphical display and analysis.

18. A method for computing a model of a heart comprising the steps of:

a) defining a set of lattice nodes;
each lattice node representing a biophysical subunit of the heart;
each node having a set of biophysical equations for computing a total node current associated with Na, Ca, and K ion transport in said biophysical subunit;
each node associated with at least five adjacent nodes;
each node coupled to neighboring nodes;
said coupling modeled as a resistance;

b) solving said set of biophysical equations to determine said node currents;

c) summing said node current to determine the voltage present at each node resulting from the depolarization of each neighboring node;

d) displaying a representation of said computed voltage;

e) adjusting the lattice defining the anatomic structure of the heart such that anatomical structural changes known to occur in the heart during said disease state;

f) using said adjusted lattice to determine the magnitude of coupling conductances between nodes of the network such that the altered structure of the heart in the disease state, as represented by the adjusted lattice, is embedded in the network model;

g) adjusting parameters of the set of state defining equations, specifying properties of biochemical cellular processes defined at each node of the lattice, to reproduce changes in these parameters known to occur in said disease state;

h) adjusting initial values of state variables, the temporal evolution of which is determined by the set of equations specifying properties of biochemical cellular processes defined at each node of the lattice, in such a way as to reproduce changes in these state variables known to occur in said disease state;

i) solving for the temporal evolution of state variables, defined at each node of the lattice;

j) storing said state variables in a computer memory for graphical display and analysis;

k) partitioning the lattice into m nodes and assigning state variable computations to one of P processing units;

l) concurrently computing state variables with the P processing units; and m) computing the temporal evolution of all state variables and storing or displaying the results.

19. A method for computing a model of a heart on multiprocessor computers consisting of a set of P processors each with local memory of size M, a communications network supporting data exchange between processors, and a global shared memory, with the method comprising the steps of:

a) defining a set of lattice nodes;
each lattice node representing a biophysical subunit of the heart;
each node having a set of biophysical equations for computing a total node current associated with ion transport in said biophysical subunit;
each node associated with at least five adjacent nodes;
each node coupled to neighboring nodes;
said coupling modeled as a resistance;

b) solving said set of biophysical equations to determine said node currents;

c) summing said node current to determine the voltage present at each node resulting from the depolarization of each neighboring node;

d) displaying a representation of said computed voltage;

e) partitioning the lattice into Q sets of nodes, referred to as node sets, in such a way that all state variable values at time t, parameters, and required temporary storage locations for any node set fits into the local memory available to any processing unit;

f) assignment of each node set to a specific processing unit and local memory associated with the specific processing unit;

g) inter-processor communication of any data required to compute new values of state variables for nodes positioned at the borders between different node sets;

h) concurrent execution on all P processors of the computations to compute new values of local state variables at time $t+\delta t$ in each of the node sets that have been assigned to processing units;

i) iteration of steps b) and d) until computation of state variable values at time $t+\delta t$, where delta t is small, and until all Q node sets are completed;

j) storage of the computed set of state variables on external storage devices for subsequent graphical display; and k) iteration of steps f)–j) until $t+\delta t$ equals some end time T.

20. A system for modeling a heart with a computer comprising:

a) a means for defining a set of nodes;
each node representing a biophysical subunit of the heart;
each node having a membrane, defining an intracellular and an extracellular space;
each node having set of biophysical equations associated with it for computing a coupling current associated with ion transport in said intracellular space;
each node having set of biophysical equations associated with it for computing a coupling current associated with ion transport in said extracellular space;

each node having a set of biophysical equations associated with it for computing a transmembrane current between the intracellular and extracellular spaces;

b) a means for defining a lattice including each of said nodes;

each node associated with a physical location in heart tissue;

substantially every node connected with at least five adjacent nodes;

each node exhibiting an anisotropic coupling with neighboring nodes reflecting the anatomic relationship between such nodes;

said coupling modeled as a coupling resistance;

c) a means for solving said set of biophysical equations to determine said node currents associated with extracellular and intracellular currents;

d) a means for summing said node current to compute the voltage present at each node resulting from the depolarization of each node and the propagation of a depolarization wave front through each node;

e) a means for displaying a representation of said computed voltage; and f) a means for modifying one or more of said biophysical equations to reflect the presence of a chemical input.

21. A system for modeling a heart with a computer comprising:

a) a means for defining a set of nodes;

each node representing a biophysical subunit of the heart;

each node having a membrane, defining an intracellular and an extracellular space;

each node having set of biophysical equations associated with it for computing a coupling current associated with ion transport in said intracellular space;

each node having set of biophysical equations associated with it for computing a coupling current associated with ion transport in said extracellular space;

each node having a set of biophysical equations associated with it for computing a transmembrane current between the intracellular and extracellular spaces;

b) a means for defining a lattice including each of said nodes;

each node associated with a physical location in heart tissue;

substantially every node connected with at least five adjacent nodes;

each node exhibiting an anisotropic coupling with neighboring nodes reflecting the anatomic relationship between such nodes;

said coupling modeled as a coupling resistance;

c) a means for solving said set of biophysical equations to determine said node currents associated with extracellular and intracellular currents;

d) a means for summing said node current to compute the voltage present at each node resulting from the depolarization of each node and the propagation of a depolarization wave front through each node;

e) a means for displaying a representation of said computed voltage; and f) a means for modifying one or more of said biophysical equations to reflect the presence of an electrical input.

22. A system for modeling a heart with a computer comprising:

a) a means for defining a set of nodes;

each node representing a biophysical subunit of the heart;

each node having a membrane, defining an intracellular and an extracellular space;

each node having set of biophysical equations associated with it for computing a coupling current associated with ion transport in said intracellular space;

each node having set of biophysical equations associated with it for computing a coupling current associated with ion transport in said extracellular space;

each node having a set of biophysical equations associated with it for computing a transmembrane current between the intracellular and extracellular spaces;

b) a means for defining a lattice including each of said nodes;

each node associated with a physical location in heart tissue;

substantially every node connected with at least five adjacent nodes;

each node exhibiting an anisotropic coupling with neighboring nodes reflecting the anatomic relationship between such nodes;

said coupling modeled as a coupling resistance;

c) a means for solving said set of biophysical equations to determine said node currents associated with extracellular and intracellular currents;

d) a means for summing said node current to compute the voltage present at each node resulting from the depolarization of each node and the propagation of a depolarization wave front through each node;

e) a means for displaying a representation of said computed voltage; and f) a means for modifying one or more of said biophysical equations to reflect the presence of a chemical compound input.

23. The model of claim 1, wherein the coupling relationships related to anisotropic anatomic structure represents fiber orientation in the heart.

24. The model of claim 1, wherein the coupling relationships related to anisotropic anatomic structure represents the spatial distribution of gap junction channels.

25. The model of claim 2, wherein the value of the anisotropic couple conductance represents in part the spatial distribution of gap junction channels.

26. A method for computing a model of a heart comprising the steps of:

a) defining a lattice of nodes with each node representing a biophysical subunit of the heart;

b) defining a set of biophysical equations associated with ion transport in the biophysical subunit;

c) defining a set of coupling equations associated with electrical coupling between neighboring nodes;

d) adjusting the equations to reflect anatomical changes known to occur in the heart during said disease state;

e) computing voltage at each node utilizing the adjusted equations; and f) displaying a representation of said computed voltage.

27. The method of claim 26, wherein the steps of computing voltage and displaying the computed voltage are repeated over time to represent the temporal evolution of the voltage.

28. The method of claim 26, wherein step d) further comprises adjusting the biophysical equations to reflect the changes in ion transport known to occur in the heart during the disease state.

29. The method of claim 26, wherein step d) further comprises adjusting the coupling equations to reflect the changes in electrical coupling between neighboring nodes known to occur in the heart during the disease state.

30. The method of claim 26, wherein step b) further comprises defining a first set of biophysical equations associated with ion transport between intracellular space and extracellular space and a second set of biophysical equations associated with ion transport in extracellular space.

31. A method of defining a model comprising the steps of:
applying nuclear magnetic resonance imaging to a biological organ to generate a data file defining tensors associated with the rate of diffusion of water molecules as determined by the anatomic structure of the physiologic organ;
applying said tensor dataset to a network to determine the magnitude of coupling conductances between nodes of the network such that the tensor information is reflected by the internodal conduction values of the network, thus embedding the anatomic characteristics of the organ in the model.

32. The model of claim 2 wherein said equations for time-varying, voltage-dependent transmembrane conductances refer to sodium (Na), potassium (K), calcium (Ca), and/or chloride (CI)) ions.

33. The method of claim 3 wherein said set of biophysical equations model the sodium (Na), potassium (K), calcium (Ca), and/or chloride (CI)) ion transport in said biophysical subunit.

34. The method of claim 17 wherein said set of biophysical equations for computing a total node current are associated with Na, Ca, and K ion species.

* * * * *